United States Patent
Sakurada (10) Patent No.: US 10,307,058 B2
(45) Date of Patent: Jun. 4, 2019

(54) OPHTHALMOLOGIC APPARATUS

(71) Applicant: TOPCON CORPORATION, Itabashi-ku (JP)

(72) Inventor: Tomohiro Sakurada, Itabashi-ku (JP)

(73) Assignee: TOPCON CORPORATION, Itabashi-ku (JP)

( * ) Notice: Subject to any disclaimer, the term of this patent is extended or adjusted under 35 U.S.C. 154(b) by 108 days.

(21) Appl. No.: 15/289,291

(22) Filed: Oct. 10, 2016

(65) Prior Publication Data

US 2017/0100033 A1    Apr. 13, 2017

(30) Foreign Application Priority Data

Oct. 13, 2015 (JP) ................................ 2015-202209

(51) Int. Cl.
  *A61B 3/14* (2006.01)
  *A61B 3/15* (2006.01)
  (Continued)

(52) U.S. Cl.
  CPC ............ *A61B 3/152* (2013.01); *A61B 3/0025* (2013.01); *A61B 3/0075* (2013.01);
  (Continued)

(58) Field of Classification Search
  CPC ......... A61B 3/09; A61B 3/024; A61B 3/0022; A61B 3/0025; A61B 3/0033;
  (Continued)

(56) References Cited

U.S. PATENT DOCUMENTS

| 2009/0207378 A1* | 8/2009 | Ito ........................ A61B 3/0075 351/245 |
| 2011/0032480 A1* | 2/2011 | Rathjen ................ A61B 3/1005 351/206 |
| 2015/0085252 A1 | 3/2015 | Fujimura et al. |

FOREIGN PATENT DOCUMENTS

| JP | 4-141135 | 5/1992 |
| JP | 9-75308 | 3/1997 |
| (Continued) | | |

OTHER PUBLICATIONS

Japanese Office Action dated Apr. 9, 2019, issued in corresponding Japanese Patent Application No. 2015-202209.

*Primary Examiner* — Mustak Choudhury
(74) *Attorney, Agent, or Firm* — Xsensus LLP (57) ABSTRACT

According to one embodiment, an ophthalmologic apparatus includes an optical system, a support, a drive unit, an alignment optical system, two or more imaging units, an analyzer, and a controller. The optical system acquires data of an eye. The support is configured to support the face of a subject. The drive unit moves the optical system and the support relative to each other. The alignment optical system projects an indicator for performing alignment of the optical system with respect to the eye onto the anterior segment of the eye. The imaging units photograph the anterior segment of the eye, onto which the indicator is being projected, substantially simultaneously from different directions. The analyzer analyzes two or more photography images captured substantially simultaneously by the imaging units to specify the position of the eye. The controller controls the drive unit based on the position specified by the analyzer.

7 Claims, 5 Drawing Sheets

(51) Int. Cl.
*A61B 3/00* (2006.01)
*A61B 3/103* (2006.01)
*A61B 3/117* (2006.01)

(52) U.S. Cl.
CPC ............ *A61B 3/0083* (2013.01); *A61B 3/103* (2013.01); *A61B 3/117* (2013.01); *A61B 3/154* (2013.01)

(58) Field of Classification Search
CPC ... A61B 3/0058; A61B 3/0075; A61B 3/0083; A61B 3/0091; A61B 3/1005; A61B 3/1025; A61B 3/10–3/18; A61B 3/102; A61B 3/103; A61B 3/107; A61B 3/112; A61B 3/113; A61B 3/117; A61B 3/145; A61B 3/152; A61B 3/154; A61B 3/1241; A61B 3/7275; G01B 11/00; G06K 9/0061; G06K 9/00604; G06K 9/2036; G06K 9/58; G06K 9/00597; A61F 9/008; A61F 9/00804; A61F 9/00806
USPC ................ 351/208–210, 211, 222, 233–243; 396/18; 606/10
See application file for complete search history.

(56) References Cited

FOREIGN PATENT DOCUMENTS

| | | |
|---|---|---|
| JP | 2011-45602 A | 3/2011 |
| JP | 2013-248376 | 12/2013 |
| JP | 2015-85081 | 5/2015 |

* cited by examiner

OPHTHALMOLOGIC APPARATUS

TECHNICAL FIELD

Embodiments described herein relate generally to an ophthalmologic apparatus for acquiring data of a subject's eye.

BACKGROUND ART

There are several types of ophthalmologic apparatuses including ophthalmologic measuring apparatuses for measuring the properties of an eye and ophthalmologic imaging apparatuses for capturing images of an eye.

Examples of the ophthalmologic measuring apparatuses include an eye refraction test apparatus (refractometer, keratometer) for measuring the refractive properties of the eye, a tonometer, a specular microscope for obtaining the properties of the cornea (corneal thickness, cell distribution, etc.), a wavefront analyzer for obtaining the aberration information of the eye by using a Hartmann-Shack sensor, and the like.

Examples of the ophthalmologic imaging apparatus include an optical coherence tomography (OCT) apparatus for capturing a tomographic image by using OCT, a fundus camera for photographing the fundus, a scanning laser ophthalmoscope (SLO) for capturing an image of the fundus by laser scanning with the use of a confocal optical system, and the like.

In ophthalmologic examination using such an apparatus, in terms of precision and accuracy of the examination, position matching (alignment) between the optical system and the eye is important. The alignment, in general, includes the operation of matching the optical axis of the optical system with the axis of the eye (XY alignment), and the operation of matching the distance between the eye and the optical system with a predetermined working distance (Z alignment).

Japanese Unexamined Patent Application Publication No. 2013-248376 discloses a technique in which the anterior segment of the eye is photographed by two or more cameras substantially simultaneously, and alignment is performed based on the position of the characteristic site (pupil center, etc.) of the anterior segment of the eye rendered in two or more captured images. Besides, Japanese Unexamined Patent Application Publication No. 2015-85081 discloses a technique in which the anterior segment of the eye is photographed from the front while a light beam is being projected on the cornea, and alignment is performed based on a bright spot image (Purkinje image) rendered in a captured anterior eye segment image.

SUMMARY OF THE INVENTION

Problems to be Solved by the Invention

Since the eye refractive power is measured by using a refractometer to prescribe glasses or contact lenses, it is necessary to measure the eye refractive power relative to the corneal vertex. Similarly, in order to ensure the accuracy of corneal curvature measurement by using a keratometer, it is necessary to perform alignment relative to the corneal vertex.

The morphology (form, shape) of the eye differs among individuals. For example, the distance from the corneal vertex to the pupil, the eccentricity condition between the cornea and the pupil are individual for every person. Conventional alignment with reference to the pupil is effective for an apparatus that acquires data of the fundus through the pupil, but is less effective for an apparatus, such as a refractometer and a keratometer, which is required to provide the alignment accuracy with respect to the cornea.

In conventional alignment based on a Purkinje image, the eye is photographed from the front. Therefore, alignment can be performed only in a state where the positions of the eye and the optical system match to some extent. In other words, wide-range alignment cannot be performed.

The object of the present invention is to provide a technology that enables alignment with respect to the cornea with high accuracy in a wide range.

Means of Solving the Problems

According to one aspect of an embodiment, an ophthalmologic apparatus includes an optical system, a support, a drive unit, an alignment optical system, two or more imaging units, an analyzer, and a controller. The optical system is configured to acquire data of an eye. The support is configured to support the face of a subject. The drive unit is configured to move the optical system and the support relative to each other. The alignment optical system is configured to project an indicator for performing alignment of the optical system with respect to the eye onto the anterior segment of the eye. The two or more imaging units are configured to photograph the anterior segment of the eye, onto which the indicator is being projected, substantially simultaneously from different directions. The analyzer is configured to analyze two or more photography images captured substantially simultaneously by the two or more imaging units to specify the position of the eye. The controller is configured to control the drive unit based on the position specified by the analyzer.

MODES FOR CARRYING OUT THE INVENTION

Exemplary embodiments of the present invention are described below. An ophthalmologic apparatus of an embodiment may be any kind of ophthalmologic measuring apparatus, any kind of ophthalmologic imaging apparatus, or any kind of multifunctional apparatus. Examples of the ophthalmologic measuring apparatus include a refractometer, keratometer, a visual function test equipment, a tonometer, and the like. Examples of the ophthalmologic imaging apparatus include an OCT apparatus, a fundus camera, an SLO, and the like.

<Configuration>

Figure 1:
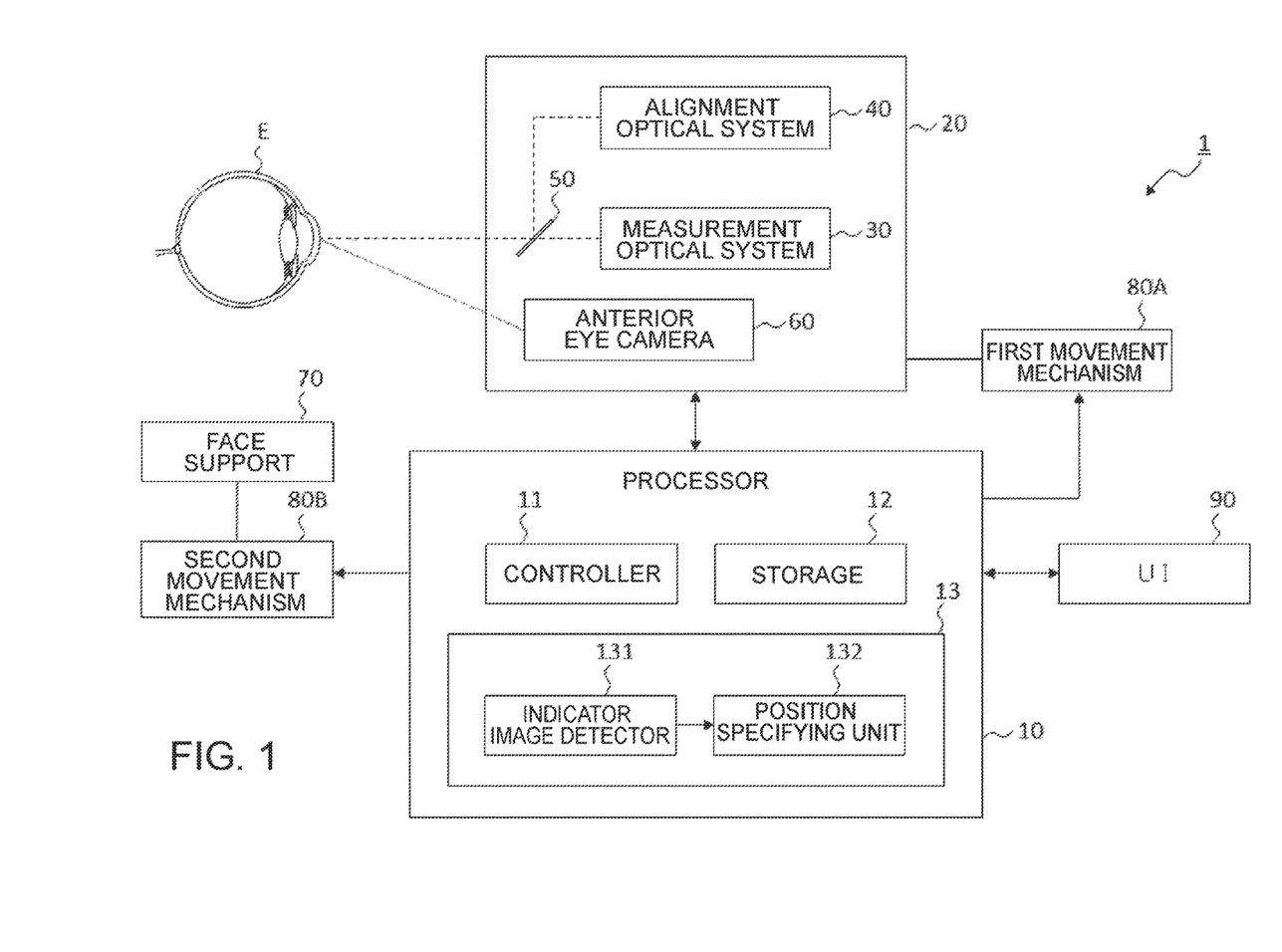
FIG. 1 is a schematic diagram illustrating an example of the configuration of an ophthalmologic apparatus according to an embodiment.

FIG. 1 illustrates an example of the configuration of an ophthalmologic apparatus. An ophthalmologic apparatus 1 has the functions of acquiring data of the subject's eye E, i.e., at least one of the function of imaging a subject's eye E and the function of measuring the properties of the subject's eye E.

The ophthalmologic apparatus 1 includes a processor 10, an optical unit 20, a face support 70, a first movement mechanism 80A, a second movement mechanism 80B, and a user interface (UI) 90. Incidentally, the ophthalmologic apparatus 1 may be provided with only one of the first movement mechanism 80A and the second movement mechanism 80B.

The optical unit 20 is provided with a measurement optical system 30, an alignment optical system 40, a beam splitter 50, and anterior eye cameras 60. The beam splitter 50 combines the optical path of the measurement optical system 30 and the optical path of the alignment optical system 40. An objective lens (not illustrated) is located between the beam splitter 50 and the subject's eye E. Two or more anterior eye cameras 60 are arranged in different positions.

(Processor 10)

The processor 10 performs various types of information processing. The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA).

For example, the processor 10 reads a program stored in a memory circuit or a storage device and executes it, thereby implementing the functions according to the embodiment. At least a part of the memory circuit or the storage device may be included in the processor 10. In addition, at least a part of the memory circuit or the storage device may be provided outside of the processor 10. Processes that can be performed by the processor 10 are described later. The processor 10 includes a controller 11, a storage 12, and a data processor 13.

(Controller 11)

The controller 11 controls each unit of the ophthalmologic apparatus 1. In particular, the controller 11 controls the optical unit the first movement mechanism 80A, and the second movement mechanism 80B. Control operations that can be performed by the controller 11 are described later.

(Storage 12)

The storage 12 stores various types of data. Examples of the data stored in the storage 12 include data (measurement data, photographic data, etc.) acquired by the measurement optical system 30 and information related to the subject and the subject's eye. The storage 12 may store a variety of computer programs and data for the operation of the ophthalmologic apparatus 1. The storage 12 stores various types of data that is used and referred to in the processes described later. The storage 12 includes the memory circuit and the storage device described above.

(Data Processor 13)

The data processor 13 performs various types of data processing. In particular, the data processor 13 analyzes photography images captured by the anterior eye cameras 60. The data processor 13 includes an indicator image detector 131 and a position specifying unit 132. Their operations are described later.

(Optical Unit 20)

The optical unit 20 houses a configuration for measuring and photographing the subject's eye E, and a configuration for the preparation thereof. The former includes the measurement optical system 30, while the latter includes the alignment optical system 40. In addition to the configuration illustrated in FIG. 1, the optical unit 20 may be provided with an optical system (observation optical system, imaging optical system, etc.) for photographing the subject's eye E from the front. The optical unit 20 may also be provided with a configuration for focusing of the measurement optical system 30 and the like. The optical unit 20 may be further provided with a light source (anterior eye illumination light source) for illuminating the anterior segment of the subject's eye E.

(Measurement Optical System 30)

The measurement optical system 30 has a configuration for measuring the properties of the subject's eye E. The measurement optical system 30 has a configuration corresponding to a function (measurement function, imaging function, etc.) offered by the ophthalmologic apparatus 1. For example, the measurement optical system 30 is provided with a light source, an optical element (optical member, optical device), an actuator, a mechanism, a circuit, a display device, a light receiving device, an image sensor, and the like. The measurement optical system 30 may have a similar configuration to that of a conventional ophthalmologic apparatus. At least part of the measurement optical system 30 may be located outside of the combined path with the alignment optical system 40. For example, if the measurement optical system 30 has a keratometer function for measuring the corneal curvature, a light source (keratometry ring light source) for projecting a ring-shaped light beam or concentric light beams onto the cornea is arranged in position immediately in front of the subject's eye E.

The measurement optical system 30 may have a configuration for providing a function associated with the examination. For example, the measurement optical system 30 may include a fixation optical system to project a target (fixation target) for fixating the subject's eye E onto the fundus of the subject's eye E.

(Alignment Optical System 40)

The alignment optical system 40 is configured to project a light beam onto the subject's eye E. Thereby, an indicator for alignment is projected onto the anterior eye segment. This indicator is detected as, for example, a Purkinje image. The alignment with the use of the indicator includes at least Z alignment in the optical axis direction (Z direction) of the measurement optical system 30. The alignment may further include XY alignment in the X direction (horizontal direction) and the Y direction (vertical direction) perpendicular to the Z direction.

The Z alignment is performed by analyzing two or more photography images substantially simultaneously captured by two or more of the anterior eye cameras 60. The XY alignment is implemented by: analyzing two or more photography images captured by two or more of the anterior eye cameras 60; or analyzing an image (front image of the anterior eye segment) obtained by the optical system (observation optical system, imaging optical system, etc.) for photographing the subject's eye E from the front.

The XY alignment based on the front image of the anterior eye segment is performed, as in the conventional manner, based on the position of the Purkinje image (indicator image), which is rendered in the front image, in the XY direction. For example, the XY alignment based on the front image of the anterior segment is performed by manually or automatically moving the optical unit 20 so as to guide the indicator image within the allowable range of the deviation of alignment (i.e., within an alignment mark). In the case of manual alignment, the controller 11 displays the front image of the anterior eye segment and the alignment mark on the user interface 90, and the user operates the user interface 90 so as to satisfy the above condition. In the case of automatic alignment, the data processor 13 calculates the deviation of the indicator image relative to the alignment mark, and the controller 11 moves the optical unit 20 in the XY direction to cancel the deviation.

(Anterior Eye Cameras 60)

As described above, the anterior eye cameras 60 are provided to two or more different positions. Each of the anterior eye cameras 60 is, for example, a video camera for capturing a moving image at a predetermined frame rate. The two or more anterior eye cameras 60 photograph the anterior eye segment from different directions substantially at the same time.

Figure 2:
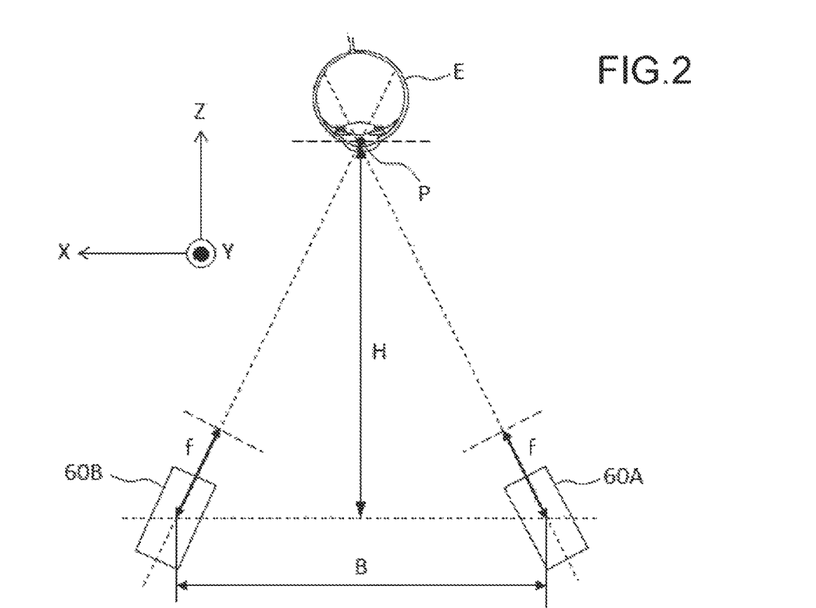
FIG. 2 is a schematic diagram for explaining the operation of the ophthalmologic apparatus of the embodiment.

As illustrated in FIG. 2, in this embodiment, the anterior eye cameras 60 include two anterior eye cameras 60A and 60B. Incidentally, FIG. 2 is a top view, in which +Y direction indicates vertically upward, and +Z direction indicates the direction of the optical axis of the measurement optical system 30, that is, a direction toward the subject's eye E from the measurement optical system 30. The anterior eye cameras 60A and 60B are each located at a position off the optical path of the measurement optical system 30. In this embodiment, the anterior eye cameras 60A and 60B are located below the optical path of the measurement optical system 30. With this, the reflected light of a light beam (indicator) projected onto the cornea is less likely to be blocked by the eyelashes, eyelids, and the like. In the following, the two anterior eye cameras 60A and 60B may sometimes be collectively represented by reference numeral 60.

There may be any number, at least two, of anterior eye cameras as long as the anterior eye segment can be substantially simultaneously photographed from two different directions. One anterior eye camera may be arranged coaxially with the measurement optical system 30.

The phrase "substantially simultaneously" indicates that the deviation in photography timings at a level where the eye movement is negligible is allowed in the photography with two or more anterior eye cameras. Therefore, it is possible for the two or more anterior eye cameras to capture images of the subject's eye E being located in the same position (being faced in the same direction).

While the two or more anterior cameras may capture still images as well as moving images, this embodiment describes moving image photography particularly in detail. In the case of moving image photography, substantially simultaneous photography of the anterior eye segment as described above can be realized by performing control for synchronizing photography start timings, controlling the frame rates or the capture timings of respective frames, or the like. On the other hand, in the case of still image photography, this can be implemented by performing control for synchronizing photography timings.

(Face Support 70)

The face support 70 includes a member for supporting the face of the subject. For example, the face support 70 includes a forehead rest on which the forehead of the subject is abutted, and a chin rest on which the chin of the subject is placed. Incidentally, the face support 70 may be provided with only one of the forehead rest and the chin rest, or it may include other members than them.

(Movement Mechanisms 80A and 80B)

The first movement mechanism 80A moves the optical unit 20 under the control of the controller 11. The first movement mechanism 80A can move the optical unit 20 three-dimensionally. For example, as in the conventional manner, the first movement mechanism 80A includes a mechanism for moving the optical unit 20 in the X direction, a mechanism for moving it in the Y direction, and a mechanism for moving it in the Z direction. The first movement mechanism 80A may include a rotating mechanism for rotating the optical unit 20 in a plane (horizontal plane, vertical plane, etc.) including the optical axis of the optical unit 20.

The second movement mechanism 80B moves the face support 70 under the control of the controller 11. The second movement mechanism 80B can move the face support 70 three-dimensionally. The second movement mechanism 80B includes, for example, a mechanism for moving the face support 70 in the X direction, a mechanism for moving it in the Y direction, and a mechanism for moving it in the Z direction. The second movement mechanism 80B may include a rotating mechanism for changing the orientation of the face support 70 (or a member included in it). If the face support 70 is provided with a plurality of members, the second movement mechanism 80B may be configured to move the members individually. For example, the second movement mechanism 80B may be configured to move the forehead rest and the chin rest independently. As described above, in general, at least one of the movement mechanisms 80A and 80B are provided.

(User Interface 90)

The user interface 90 provides functions to exchange information between the ophthalmologic apparatus 1 and the user, such as display of information, input of information, input of an operation instruction, and the like. The user interface 90 provides output function and input function. Examples of configurations that provide the output function include a display device such as a flat panel display, an audio output device, a print output device (printer), a data writer for writing data to a recording medium, and the like. Examples of configurations that provide the input function include an operation lever, a button, a key, a pointing device, a microphone, a data reader, and the like. The user interface 90 may include a device having the output function and the input function integrated together, such as a touch panel display. The user interface 90 may include a graphical user interface (GUI) input and output information.

(Data Processor 13)

Described below are details of the data processor 13. As described above, the data processor 13 includes the indicator image detector 131 and the position specifying unit 132.

(Indicator Image Detector 131)

The indicator image detector 131 analyzes two photography images captured substantially simultaneously by the anterior eye cameras 60A and 60B to detect an indicator image that is rendered in each of the photography images. When the anterior eye cameras 60A and 60B capture moving images, the indicator image detector 131 detects an indicator image from each frame. The indicator image detector 131 detects the indicator image by analyzing the pixel values of the photography image. If the photography image is an intensity image (luminance image), the indicator image detector 131 specifies an image area (pixels) corresponding to the indicator image based on the distribution of luminance values in the photography image. This process includes, for example, a process of selecting a pixel having a higher luminance value than a predetermined threshold value. If the photography image is a color image, the indicator image detector 131 performs, for example, a process of selecting a pixel having a higher luminance value than a predetermined threshold value, or a process of selecting a pixel that represents a predetermined color.

(Position Specifying Unit 132)

The position specifying unit 132 specifies the position of the subject's eye E based on two indicator images detected from two photography images captured substantially simultaneously by the anterior eye cameras 60A and 60B. The position specifying unit 132, at least, calculates the distance between the measurement optical system 30 and the subject's eye E in the Z direction. Z alignment is performed based on the calculation result. Further, the position specifying unit 132 may calculate a deviation between the measurement optical system 30 and the subject's eye E in the XY directions. The XY alignment is performed based on the calculation result.

The process performed by the position specifying unit 132 is described with reference to FIG. 2. FIG. 2 is a top view illustrating the positional relationship between the subject's eye E and the anterior eye cameras 60A and 60B. Reference letter "B" represents the distance (baseline length) between the two anterior eye cameras 60A and 60B in the XY direction. Reference letter "H" represents the distance (indicator image distance) between the baseline, connecting the two anterior eye cameras 60A and 60B, and the indicator image P. Reference letter "f" represents the distance (screen distance) between each of the anterior eye cameras 60A and 60B and the screen plane. In general, when an indicator light beam is projected as a parallel light beam onto the subject's eye E, the indicator image (Purkinje image) P is formed in a position displaced from the corneal surface by half of the corneal radius of curvature of the subject's eye E in the +Z direction.

In this arrangement, the resolution of photography images captured by the anterior eye cameras 60A and 60B is expressed by the following equations. In the following equations, $\Delta p$ represents the pixel resolution.

Resolution in the *XY* direction: $\Delta XY = H \times \Delta p / f$

Resolution in the Z direction: $\Delta Z = H \times H \times \Delta p / (B \times f)$ The position specifying unit 132 applies a known triangulation method, with consideration of the positional relationship illustrated in FIG. 2 (and FIG. 1), to the positions of the two anterior eye cameras 60A and 60B (known) and the positions of the indicator image P in two photography images, thereby specifying the position of the indicator image P, i.e., the position of the subject's eye E. The position to be specified includes at least a position in the Z direction, and it may further include a position in the XY direction.

The position of the subject's eye E specified by the position specifying unit 132 is sent to the controller 11. Based on the position of the subject's eye E in the Z direction, the controller 11 controls at least one of the first and second movement mechanisms 80A and 80B so as to match the distance between the subject's eye E and the measurement optical system 30 in the Z direction with the working distance. Besides, based on the position of the subject's eye E in the XY direction, the controller 11 controls at least one of the first and second movement mechanisms 80A and 80B so as to match the optical axis of the measurement optical system 30 and the axis of the subject's eye E with each other. Incidentally, the working distance means a predetermined distance between the subject's eye E and the measurement optical system 30 to perform measurement with the measurement optical system 30.

As described above, the position specifying unit 132 can determine the position of the indicator image P (Purkinje image) as the position of the subject's eye E (the approximate position of the subject's eye E). Further, based on the position of the indicator image P specified and the corneal radius of curvature measured separately, the position specifying unit 132 can determine the position of the cornea (corneal vertex) of the subject's eye E. In a state where XYZ alignments are correct, the corneal vertex is considered as being located in a position displaced from the indicator image P by half of the corneal radius of curvature in the −Z direction. Thus, the Z coordinate value of the corneal vertex (XYZ coordinate values including the same) can be obtained by subtracting a value of half of the corneal radius of curvature from the Z coordinate value of the indicator image P.

The measurement of the corneal radius of curvature is performed by using a keratometer, a corneal topographer, or the like. If the ophthalmologic apparatus 1 is not provided with the function of measuring the corneal radius of curvature, the measured value of the corneal radius of curvature obtained in the past is fed to the ophthalmologic apparatus 1. The position specifying unit 132 obtains the corneal vertex position by using the measured value. On the other hand, when the ophthalmologic apparatus 1 has the function of measuring the corneal radius of curvature, for example, the corneal radius of curvature is measured after the implementation of alignment, and alignment can be performed again by using the measured value obtained. If the ophthalmologic apparatus 1 has the function of measuring the corneal radius of curvature, it is also possible to use the measured value of the corneal radius of curvature obtained in the past.

(Other Examples of Processes)

Described below are other examples of processes for specifying the position of the subject's eye E on the basis of two photography images captured by the anterior eye cameras 60A and 60B.

Figure 3A:
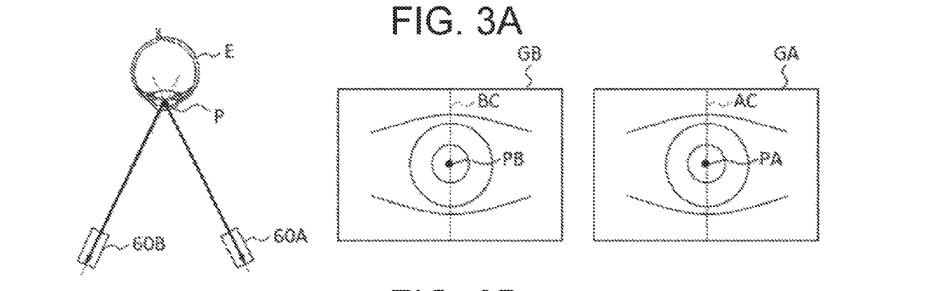
FIG. 3A is a schematic diagram for explaining the operation of the ophthalmologic apparatus of the embodiment.

In FIG. 3A, the left diagram illustrates a state where the XYZ alignments match, and the right diagram illustrates two photography images obtained at that time. If all the XYZ alignments match with respect to the indicator image P, i.e., if the indicator image P is located in the position (optical axis intersecting position) where the optical axis of the right anterior eye camera 60A and the optical axis of the left anterior eye camera 60B intersect with each other, a photography image GA is captured by the right anterior eye camera 60A, and a photography image GB is captured by the left anterior eye camera 60B, in the photography image GA, an indicator image PA is located at a center position AC (or the vicinity thereof) of a frame in the lateral direction (right-left direction). Similarly, in the photography image GB, an indicator image PB is located at a center position BC (or the vicinity thereof) of a frame in the lateral direction.

Figure 3B:
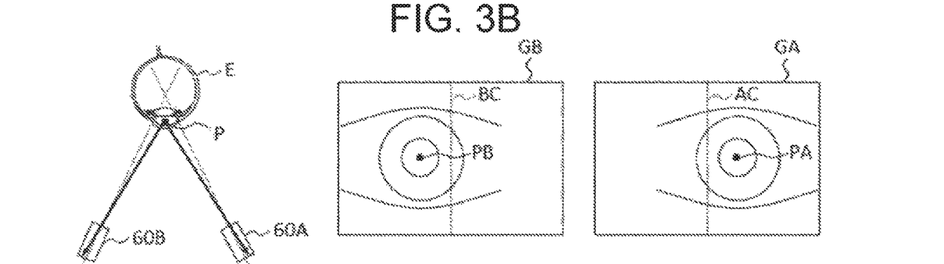
FIG. 3B is a schematic diagram for explaining the operation of the ophthalmologic apparatus of the embodiment.

FIG. 3B illustrates a case where the subject's eye E is too close to the ophthalmologic apparatus 1, i.e., where the indicator image P is located on the side of the ophthalmologic apparatus 1 relative to the optical axis intersecting position. In the photography image GA captured by the right anterior eye camera 60A, the indicator image PA is located on the right side of the center position AC. Meanwhile, in the photography image GB captured by the left anterior eye camera 60B, the indicator image PB is located on the left side of the center position BC. In other words, the interval between the two indicator images PA and PB in the two photography images GA and GB becomes wide in this case.

Figure 3C:
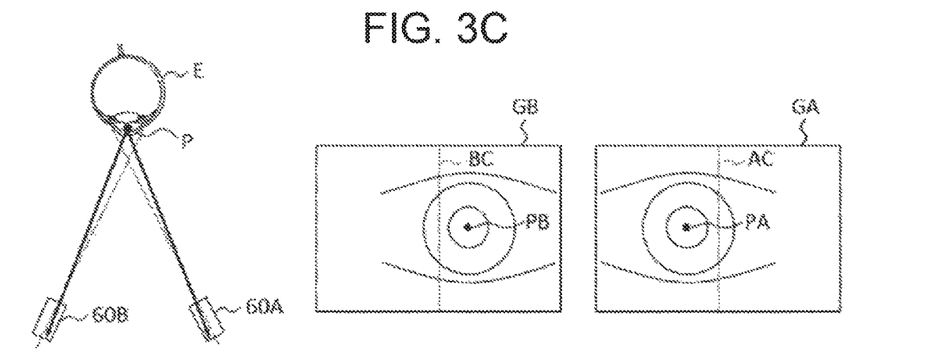
FIG. 3C is a schematic diagram for explaining the operation of the ophthalmologic apparatus of the embodiment.

On the other hand, FIG. 3C illustrates a case where the subject's eye E is too far from the ophthalmologic apparatus 1. In the photography image GA captured by the right anterior eye camera 60A, the indicator image PA is located on the left side of the center position AC. Meanwhile, in the photography image GB captured by the left anterior eye camera 60B, the indicator image PB is located on the right side of the center position BC. In other words, the interval between the indicator images PA and PB in the two photography images GA and GB becomes narrow in this case.

In this manner, the relative position between the two indicator images PA and PB in the two photography images GA and GB vary according to the state of the Z alignment. The deviation direction in the Z alignment (near/far) appears as the direction of change (increase in interval/decrease in interval) in the relative position between the two indicator images PA and PB. In addition, the amount of deviation in the Z alignment appears as the amount of change in the relative position between the two indicator images PA and PB.

Information that represents such relationship is stored in the position specifying unit 132 (or the storage 12) in advance. In the information, for example, relative positions (interval values) between the two indicator images and deviation directions and deviation amounts in the Z alignment are associated with each other. First, the position specifying unit 132 obtains the positions of (the relative position between) the two indicator images PA and PB detected from the two photography images GA and GB. The position specifying unit 132 then obtains the deviation direction and deviation amount in the Z alignment corresponding to the obtained positions of the two indicator images PA and PB with reference to the abovementioned information stored.

Figure 4A:
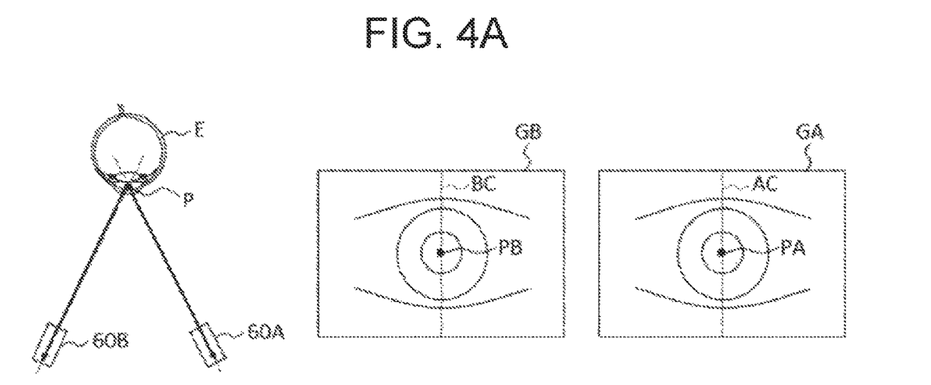
FIG. 4A is a schematic diagram for explaining the operation of the ophthalmologic apparatus of the embodiment.

As in FIG. 3A, in FIG. 4A, the left diagram illustrates a state where the XYZ alignments match, and the right diagram illustrates two photography images obtained at that time.

Figure 4B:
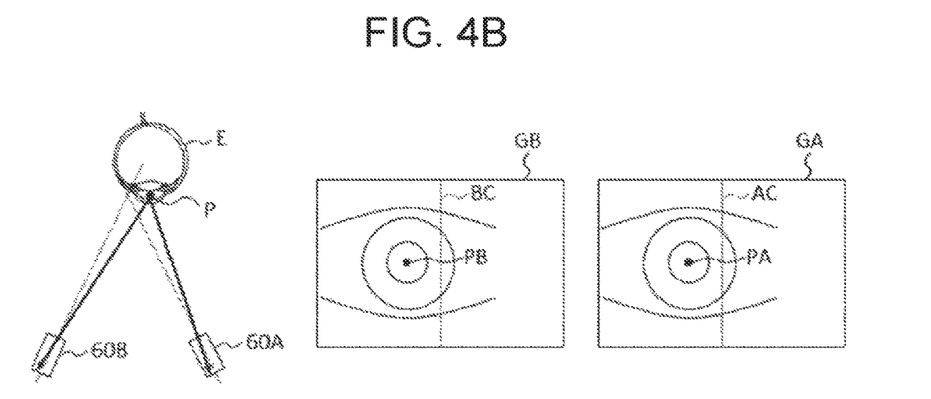
FIG. 4B is a schematic diagram for explaining the operation of the ophthalmologic apparatus of the embodiment.

FIG. 4B illustrates a case where the subject's eye E is deviated to the right side with respect to the anterior eye cameras 60A and 60B, i.e., a case where the indicator image P is located on the right side of the optical axis intersecting position of the anterior eye cameras 60A and 60B. In the photography image GA captured by the right anterior eve camera 60A, the indicator image PA is located on the left side of the center position AC. Similarly, in the photography image GB captured by the left anterior eye camera 60B, the indicator image PB is located on the left side of the center position BC. In other words, the interval between the two indicator images PA and PB in the two photography images GA and GB is substantially unchanged, and the two indicator images PA and PB are deviated in the left direction by substantially the same distance.

Figure 4C:
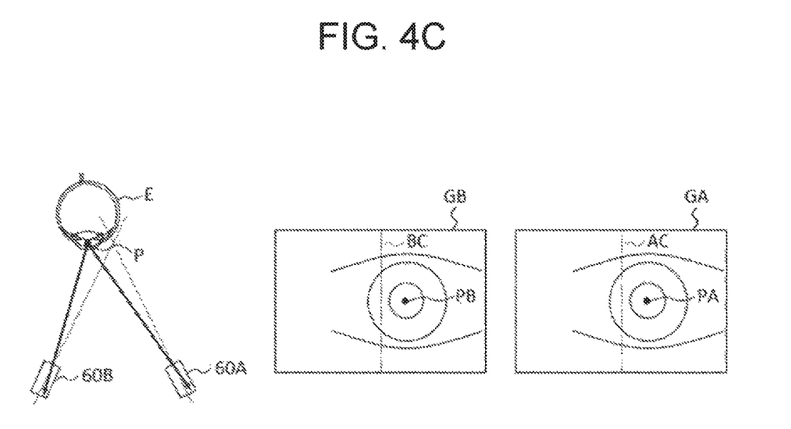
FIG. 4C is a schematic diagram for explaining the operation of the ophthalmologic apparatus of the embodiment.

On the other hand. FIG. 4C illustrates a case where the subject's eye E is deviated to the left side with respect to the anterior eye cameras 60A and 60B. In the photography image GA captured by the right anterior eye camera 60A, the indicator image PA is located on the right side of the center position AC. Similarly, in the photography image GB captured by the left anterior eye camera 60B, the indicator image PB is located on the right side of the center position BC. In other words, the interval between the two indicator images PA and PB in the two photography images GA and GB is substantially unchanged, and the two indicator images PA and PB are deviated in the right direction by substantially the same distance.

In this manner, the two indicator images PA and PB in the two photography images GA and GB are deviated in the same direction by substantially the same distance according to the state of the X alignment. The deviation direction (right/left) in the X alignment appears as the direction of the integral deviation of the two indicator images PA and PB. In addition, the amount of deviation in the X alignment appears as the amount of the integral deviation of the two indicator images PA and PB.

Information that represents such relationship is stored in the position specifying unit 132 (or the storage 12) in advance. In the information, for example, deviations (deviation directions and deviation amounts) of the two indicator images in the lateral direction with respect to the frame center are associated with deviation directions and deviation amounts of the X alignment. First, the position specifying unit 132 obtains the positions of (the relative position between) the two indicator images PA and PB detected from the two photography images GA and GB, and obtains the deviation directions and the deviation amounts of the indicator images PA and PB with respect to the center positions AC and BC, respectively. The position specifying unit 132 then obtains the deviation direction and deviation amount in the X alignment corresponding to the obtained deviation directions and deviation amounts of the two indicator images PA and PB with reference to the abovementioned information stored.

Similarly, the deviation in the Y alignment is calculated based on the correspondence between the deviations (deviation directions and deviation amounts) of the two indicator images in the vertical direction with respect to the frame center, and the deviation directions as well as the deviation amounts in the Y alignment.

(Alignment Based on the Characteristic Site of the Anterior Eye Segment)

As disclosed in Japanese Unexamined Patent Application Publication No. 2013-248376, the ophthalmologic apparatus 1 may be configured to perform alignment based on the position of the characteristic site of the anterior eye segment. In this case, the data processor 13 analyzes two photography images captured substantially simultaneously by the anterior eye cameras 60A and 60B, and thereby specifies a characteristic position corresponding to the characteristic site of the anterior eye segment. The characteristic site of the anterior eye segment is, for example, the center of the pupil. Besides, the data processor 13 specifies the position of the subject's eye E based on the characteristic position specified. In this example, the position of the center of the pupil is approximated to the position of the subject's eye E. By using the distance between the corneal vertex and the pupil of the subject's eye E, or the distance between the corneal vertex and the pupil of the standard eye (eye model, mean value, etc.), the position of the corneal vertex can be obtained as the position of the subject's eye E. The distance in the subject's eye E is measured by using, for example, OCT or an ultrasonic measuring apparatus.

<Operations>

Figure 5:
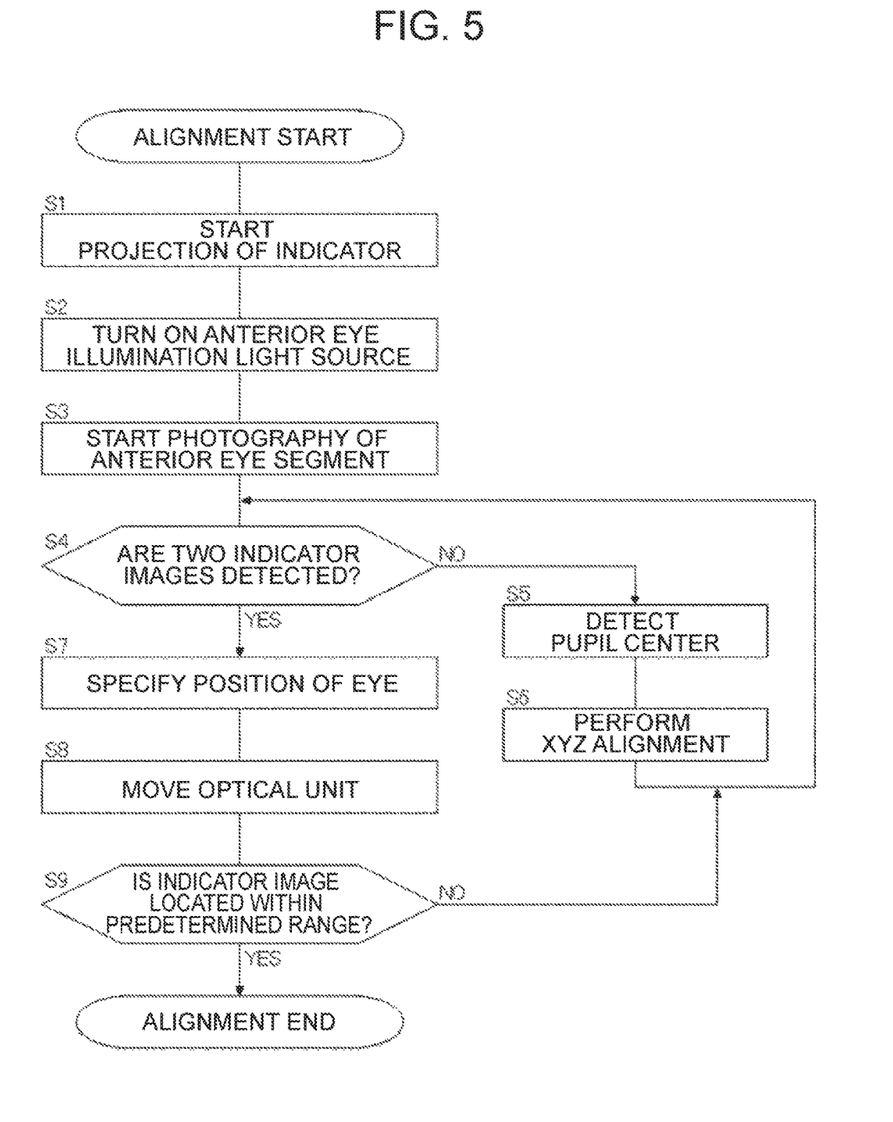
FIG. 5 is a flowchart illustrating an example of the operation of the ophthalmologic apparatus of the embodiment.

A description is given of the operations of the ophthalmologic apparatus 1. FIG. 5 illustrates an example of alignment performed by the ophthalmologic apparatus 1.

(S1: Start Projection of Indicator)

In response to an instruction to start alignment from the user or the controller 11, the controller controls the alignment optical system 40 to project an indicator for the alignment onto the anterior segment of the subject's eye E. The projection of the indicator is continued, for example, until an instruction to finish the alignment is given.

(S2: Turn on Anterior Eye Illumination Light Source)

The controller 11 turns on the anterior eye illumination light source mentioned above. The anterior eye illumination light source is on until, for example, until an instruction to finish the alignment is given.

(S3: Start Photography of Anterior Eye Segment)

The anterior eye cameras 60A and 60B start capturing moving images of the anterior segment of the eye. Each of the anterior eye cameras 60A and 60B captures photography images (frames) at a predetermined frame rate. The photography images are sequentially input to the data processor 13.

(S4: Are Two Indicator Images Detected?)

In order to detect indicator images, the indicator image detector 131 analyzes the two photography images GA and GB captured substantially simultaneously by the anterior eye cameras 60A and 60B. If no indicator image is detected from at least one of the two photography images GA and GB (S4: NO), the process proceeds to step S5. On the other hand, if an indicator image is detected from both of two photography images GA and GB (S4: YES), the process proceeds to step S7.

(S5: Detect Pupil Center)

If no indicator image is detected from at least one of the two photography images GA and GB (S4: NO), the data processor 13 analyzes each of two or more photography images substantially simultaneously captured by the anterior eye cameras 60A and 60B to specify a characteristic position corresponding to the pupil center of the anterior segment of the subject's eye E. The two or more photography images analyzed here may be the two photography images analyzed in step S4, or they may be newly acquired two photography images.

(S6: Perform XYZ Alignment)

The data processor 13 specifies the position of the subject's eye E based on the characteristic position specified in step S5. Then, the controller 11 controls the first movement mechanism 80A (and/or the second movement mechanism 80B) based on the specified position. Processes in steps S5 and S6 are performed in the manner disclosed in Japanese Unexamined Patent Application Publication No. 2013-248376. After the optical unit 20 (and/or the face support 70) is moved, the process returns to step S4.

Steps S4 to S6 are repeated until an indicator image is detected from both of the two photography images GA and GB in step S4. Incidentally, it is possible to output an alarm or shift to manual alignment when the number of repetitions reaches a predetermined number of times, or when the repetitive process has continued for a predetermined period of time.

(S7: Specify Position of Eye)

If an indicator image is detected from both of the two photography images GA and GB (S4: YES), the position specifying unit 132 specifies the position of the subject's eye E based on the two indicator images PA and PB detected.

(S8: Move Optical Unit)

The controller 11 controls the first movement mechanism 80A (and/or the second movement mechanism 80B) based on the position of the specified eye E specified in step S7. In this control, for example, the optical unit 20 (and/or the face support 70) is moved to cancel the deviation between the specified position of the subject's eye E and the center position of a predetermined range that represents an allowable range of alignment deviation.

(S9: Is indicator Image Located Within Predetermined Range?)

If an indicator image detected after the movement of the optical unit 20 in step S8 is not located within the predetermined range (S9: NO), the process returns to step S4. Steps S4 to S9 are repeated until the indicator image is determined to be located within the predetermined range in step S9. Incidentally, it is possible to output an alarm or shift to manual alignment when the number of repetitions reaches a predetermined number of times, or when the repetitive process has continued for a predetermined period of time.

When the indicator image is determined to be located within the predetermined range in step S9 (S9: YES), the alignment ends. Then, after further preparation operation such as focusing and the like is performed as required, the measurement (imaging) of the subject's eye E is performed with the measurement optical system 30.

<Operation and Effects>

Described below are the operations and effects of an ophthalmologic apparatus according to an embodiment.

According to an embodiment, an ophthalmologic apparatus includes an optical system (e.g., the measurement optical system 30), a support (e.g., the face support 70), a drive unit (e.g., the first movement mechanism 80A and/or the second movement mechanism 80B), an alignment optical system (e.g., the alignment optical system 40), two or more imaging units (e.g., the anterior eye cameras 60A and 60B), an analyzer (e.g., the data processor 13), and a controller (e.g., the controller 11).

The optical system is configured to acquire data of an eye. The support is configured to support the face of a subject. The drive unit is configured to move the optical system and the support relative to each other. The alignment optical system is configured to project an indicator for performing alignment of the optical system with respect to the eye onto the anterior segment of the eye. The two or more imaging units are configured to be capable of photographing the anterior segment of the eye, onto which the indicator is being projected, substantially simultaneously from different directions. The analyzer is configured to analyze two or more photography images captured substantially simultaneously by the two or more imaging units to specify the position of the eye. The controller is configured to control the drive unit based on the position of the eye specified by the analyzer.

In an embodiment, the analyzer may include an indicator image detector (e.g., the indicator image detector 131) and a position specifying unit (e.g., the position specifying unit 132). The indicator image detector is configured to analyze each of the two or more photography images captured substantially simultaneously by the two or more imaging units, and thereby detecting an image of the indicator. The position specifying unit is configured to specify the position of the eye based on two or more images detected from the two or more photography images. The controller is configured to control the drive unit based on the position of the eye thus specified.

According to the embodiment, alignment can be performed by using two or more photography images of the anterior eye segment captured substantially simultaneously by the two or more imaging units. With this, alignment can be performed in a wider range compared to the case of using a front image of the anterior eye segment. Further, according to the embodiment, alignment can be performed with reference to the position of the indicator projected onto the anterior eye segment. This increases the alignment accuracy with respect to the cornea as compared to the case where alignment is performed with reference to the pupil center, or the like. Thus, it is possible to perform alignment with respect to the cornea in a wide range with high accuracy.

In an embodiment, the position specifying unit may be configured to calculate a distance between the optical system and the subject's eye in the optical axis direction of the optical system (in the Z direction) based on the relative position between the two or more images in the two or more photography images of the anterior eye segment captured substantially simultaneously. In this case, based on the distance in the Z direction calculated, the controller can control the drive unit to match the distance between the eye and the optical system in the Z direction with a predetermined working distance. In other words, the ophthalmologic apparatus of the embodiment may be configured to perform such Z alignment.

In an embodiment, the position specifying unit may be configured to calculate a deviation between the eye and the optical system in a direction perpendicular to the Z direction (in the XY direction) based on the positions of the two or more images in the two or more photography images of the anterior eye segment captured substantially simultaneously. In this case, the controller can control the drive unit to match the optical axis of the optical system with the axis of the eye based on the deviation in the XY direction calculated. In other words, the ophthalmologic apparatus of the embodiment may be configured to be capable of performing such XY alignment.

In an embodiment, if no indicator image is detected from at least one of the two or more photography images of the anterior eye segment captured substantially simultaneously, the following processes may be performed. First, the analyzer analyzes each of two or more photography images captured substantially simultaneously by the two or more imaging units, and thereby specifying the characteristic position corresponding to the characteristic site (pupil center, etc.) of the anterior eye segment. Further, the analyzer specifies the position of the eye based on the characteristic position specified. Then, the controller controls the drive unit based on the position of the eye thus specified. That is, the ophthalmologic apparatus of the embodiment may be configured to perform XYZ alignment as disclosed in Japanese Unexamined Patent Application Publication No. 2013-248376 when no indicator image is detected from at least one of the two or more photography images of the anterior eye segment captured substantially simultaneously.

After the XYZ alignment is performed with reference to such characteristic site, the indicator image detector analyzes two or more photography images newly captured by the two or more imaging units, and thereby detecting an indicator image again. Then, alignment can be performed based on the image of the indicator in the manner described above. That is, when no indicator image is detected from at least one of the two or more photography image of the anterior eye segment captured substantially simultaneously, rough alignment may be performed by using the technique disclosed in Japanese Unexamined Patent Application Publication No. 2013-248376. After that, process may proceed to fine alignment according to the present embodiment.

<Modification>

The embodiments described above are mere examples for embodying or carrying out the present invention, and therefore susceptible to several modifications and variations (omission, substitution, addition, etc.), all coming within the scope of the invention.

When a plurality of measurements (a plurality of imaging processes) is preformed sequentially, alignment can be performed immediately before each of the measurements. For example, when the corneal curvature measurement (keratometry measurement), the eye refractive power measurement (refraction measurement), and the subjective examination (visual acuity test) are performed in this order, alignment can be performed before the keratometry measurement, between the keratometry measurement and refraction measurement, and between the refraction measurement and the subjective examination. Alternatively, alignment may be performed immediately before a part of the plurality of measurements.

In one modification of the embodiment, the Z alignment may be performed in the method of the embodiment, and the XY alignment may be performed by another method. For example, the technique disclosed in Japanese Unexamined Patent Application Publication No. 2013-248376 may be applied to the XY alignment. That is, based on two or more photography images of the anterior eye segment captured substantially simultaneously, the XY alignment can be performed with reference to the pupil. Alternatively, if there is provided an observation optical system for photographing the eye from the front, known XY alignment can be performed based on an indicator image (bright spot image), the position of the pupil center, or the like in the front image of the anterior segment captured by the observation optical system.

There is a measurement method of acquiring the properties of the eye based on a pattern image projected onto the anterior eye segment. A typical example of this is the keratometry measurement. In the keratometry measurement, a circular or concentric pattern image (keratometry ring image) is projected onto the cornea by using a keratometry ring light source arranged immediately in front of the subject's eye E, and the corneal shape (corneal curvatur is determined based on the shape of the keratometry ring image. Such measurement technique is performed, in general, by using the observation optical system (front image). However, in the embodiment, the properties of the eye may be obtained based on the pattern image rendered in a photography image captured by any (one or more) of the two or more imaging units.

What is claimed is:

1. An ophthalmologic apparatus comprising:
   a measurement optical system including a light source and an optical element for performing at least one of imaging an eye and measuring a property of the eye;
   a support configured to support face of a subject;
   a movement mechanism that moves the measurement optical system and the support relative to each other;
   an alignment optical system including a light beam projector that projects an indicator for performing alignment of the measurement optical system with respect to the eye onto an anterior segment of the eye;
   two or more imagers configured to photograph the anterior segment of the eye, onto which the indicator is being projected, substantially simultaneously from different directions;
   a data processor including circuitry configured to operate as an analyzer that analyzes two or more photography images captured substantially simultaneously by the two or more imagers to specify position of the eye, the analyzer including
     an indicator image detector that analyzes each of the two or more photography images to detect Purkinje images as images of the indicator, and
     a position specifier that specifies a position of a corneal vertex as the position of the eye based on positions of the detected Purkinje images detected from the two or more photography images, and a corneal radius of curvature; and a controller configured to control the movement mechanism based on the position specified by the analyzer.

2. The ophthalmologic apparatus of claim 1, wherein the position specifier calculates a distance between the eye and the measurement optical system in a direction perpendicular to a baseline connecting the two or more imagers based on positions of the images of the indicator represented in the two or more photography images respectively.

3. The ophthalmologic apparatus of claim 2, wherein the controller is configured to control the movement mechanism to match the distance between the eye and the measurement optical system in the direction perpendicular to the baseline connecting the two or more imagers with a predetermined working distance based on the distance calculated by the position specifier.

4. The ophthalmologic apparatus of claim 2, wherein the position specifier calculates a deviation between the eye and the measurement optical system in a direction perpendicular to the optical axis direction based on positions of the two or more images in the two or more photography images.

5. The ophthalmologic apparatus of claim 4, wherein the controller is configured to control the movement mechanism to match optical axis of the measurement optical system with axis of the eye based on the deviation calculated by the position specifier.

6. The ophthalmologic apparatus of claim 1, wherein
when no image of the indicator is detected from at least one of the two or more photography images, the analyzer in the data processor including circuitry analyzes each of two or more photography images captured substantially simultaneously by the two or more imagers to specify a characteristic position corresponding to a characteristic site of the anterior segment of the eye, and specifies position of the eye based on the characteristic position specified, and the controller is configured to control the movement mechanism based on the position specified based on the characteristic position.

7. The ophthalmologic apparatus of claim 6, wherein after the movement mechanism is controlled based on the characteristic position, the indicator image detector analyzes two or more photography images newly captured by the two or more imagers to detect images of the indicator again.

* * * * *